United States Patent
Teraoka

(10) Patent No.: US 6,823,040 B1
(45) Date of Patent: Nov. 23, 2004

(54) X-RAY INSPECTION METHOD AND APPARATUS USED FOR THE SAME

(75) Inventor: Akira Teraoka, Osaka (JP)

(73) Assignee: Techno Enami Corporation, Osaka (JP)

( * ) Notice: Subject to any disclaimer, the term of this patent is extended or adjusted under 35 U.S.C. 154(b) by 0 days.

(21) Appl. No.: 09/533,778

(22) Filed: Mar. 24, 2000

(30) Foreign Application Priority Data

Mar. 25, 1999 (JP) .......................................... 11-082501

(51) Int. Cl.[7] .............................................. A61B 6/00
(52) U.S. Cl. ........................................ 378/25; 378/21
(58) Field of Search .............................. 378/21, 11, 23, 378/24, 25, 26, 58; 250/559.44

(56) References Cited

U.S. PATENT DOCUMENTS

| | | | | |
|---|---|---|---|---|
| 4,455,668 A | * | 6/1984 | Warden | 378/21 |
| 4,829,547 A | * | 5/1989 | Mustain | 378/21 |
| 4,852,131 A | * | 7/1989 | Armistead | 378/4 |
| 4,853,540 A | * | 8/1989 | Nakajima | 250/583 |
| 5,388,136 A | * | 2/1995 | Halliday et al. | 378/58 |
| 5,719,952 A | * | 2/1998 | Rooks | 378/22 |
| 6,043,876 A | * | 3/2000 | Holliday et al. | 356/237.1 |
| 6,134,013 A | * | 10/2000 | Sirat et al. | 356/364 |
| 6,177,682 B1 | * | 1/2001 | Bartulovic et al. | 250/559.12 |

FOREIGN PATENT DOCUMENTS

| | | | |
|---|---|---|---|
| JP | 10-239253 | * | 9/1998 |
| JP | 2000-275191 | * | 10/2000 |

* cited by examiner

*Primary Examiner*—Edward J. Glick
*Assistant Examiner*—Hoon Song
(74) *Attorney, Agent, or Firm*—Wenderoth, Lind & Ponack, L.L.P.

(57) ABSTRACT

X-ray inspection of mounting conditions of electronic devices such as BGAs and CSPs, which are steadily getting smaller and having higher densities on circuit boards, particularly open solder ball connection and the like, can be precisely judged. An X-ray source applies X-rays and an X-ray detecting device to detect X-rays are arranged so as to face each other with a sample therebetween. X-ray emitted from the X-ray source pass through the sample and are detected in the X-ray detecting device. An X-ray incidence plane in the X-ray detecting device is arranged so as to be parallel to an axis S. A swinging device swings or orbits the X-ray-detecting device about the axis S as a central axis while the X-ray incidence plane is kept facing in the same direction all of the time. A rotating device rotates or pivots the X-ray source about the axis S in synchronization with the X-ray detecting device.

10 Claims, 14 Drawing Sheets

X-RAY INSPECTION METHOD AND APPARATUS USED FOR THE SAME

BACKGROUND OF THE INVENTION

1. Field of the Invention

The present invention relates to a method of X-ray inspection and an apparatus used for the method and, more particularly, to a method of X-ray inspection for inspecting the mounting condition (connection) of electronic devices such as BGAs (Ball Grid Arrays) and CSPs (Chip Scale Packages) which are small in size and have high densities on boards and the like using X-rays and an apparatus used for the method.

2. Description of the Relevant Art

In recent years, the performance of cellular phones, personal computers, video and audio equipment and the like has been getting remarkably higher. What makes it possible is IC packaging technology, which is at the core of the high performance. The density of packages for mounting IC chips and the speed of signal processing have been getting higher.

In particular, array packages such as BGAs and CSPs, which have recently appeared as a means of enabling an innovative packaging technology, and which are effective in having more terminals, have attracted attention.

However, though array packages such as BGAs are excellent at having more terminals, it is difficult to judge whether the mounting condition of an array package on a printed circuit board is good or bad by an optical or a laser visual inspection, since, on account of the construction thereof, the connecting portion of the package and the printed circuit board is hidden from sight by the package itself when it is mounted on the printed circuit board. In the case of fine-pitch packages, it is difficult to accurately pinpoint the location of defects even by an electrical test.

FIG. 1 is a perspective view diagrammatically showing the state of an example of a BGA 1 seen from the side of terminals. FIG. 2 is a perspective view diagrammatically showing a printed circuit board 2 in a situation where the BGA 1 shown in FIG. 1 is mounted thereon. As is obvious from FIG. 2, it is extremely difficult to judge by their appearance whether the connection condition of solder balls 1a, except for those at the outermost periphery of the BGA 1 and the printed circuit board 2, is good or bad when the BGA 1 is mounted on the printed circuit board 2.

Present exemplary techniques of inspecting the connection condition of an array package such as a BGA and a printed circuit board, include a system wherein various and precise two- or three-dimensional perspective images of the connecting portion, seen from a given direction, are obtained (radiography), and a system wherein sectional images of the connecting portion taken as if it had been sliced on a plane parallel to the main surface of the printed circuit board (so-called transverse sectional images) are obtained (sectional radiography).

Radiography uses an X-ray three-dimensional inspection apparatus, for example. FIG. 3 shows examples of X-ray photographs of the connecting portion taken using the X-ray three-dimensional inspection apparatus for radiography.

As is obvious from FIG. 3, by utilizing the X-ray three-dimensional inspection apparatus, the inner shape, which cannot be observed from the outside, can be observed as perspective images. Therefore, even if the inner shape is complicated, whether the inner condition is good or bad can be judged with fair precision.

However, it is difficult to precisely detect the open state of terminals (solder balls) which users like to inspect most in the mounting of array packages such as BGAs and CSPs, forming the heart of the latest high-density packaging. FIG. 4 diagrammatically shows an example of the open state of solder balls.

By obtaining transverse sectional (horizontal slice) images of the connecting portion at two or more vertical positions thereof using sectional radiography, and measuring and comparing the degrees of shadow, the inner shape thereof can be inspected to some extent.

However, it is essentially difficult to precisely detect open terminals (solder balls) in the situation where an array package such as a BGA or a CSP is mounted on a printed circuit board through slice-shaped sectional images of transverse sectional images, because it means trying to detect an open state, which appear in a direction vertical to the main surface of a printed circuit board from the horizontal direction.

SUMMARY OF THE INVENTION

The present invention was achieved in order to solve the above problems. It is an object of the present invention to provide a method of and apparatus for X-ray inspection whereby the condition of electronic equipment, like the mounting condition of electronic devices such as BGAs and CSPs, which are steadily getting smaller and reaching higher densities on boards, and particularly open terminals, can be precisely judged.

As described above, hitherto the connecting portion of an array package, such as a BGA and a printed circuit board, hidden from sight by the package itself, has been inspected using perspective images from horizontal or oblique directions (see FIG. 3) or transverse sectional images. But it is essentially impossible to precisely detect opens terminals (solder balls) by these inspection systems.

The present inventor noticed that open solder balls (see FIG. 4) are problems essentially appearing in a direction vertical to a BGA or the main surface of a printed circuit board, rather than in a direction parallel thereto, and appreciated that the detection of open solder balls can be certainly carried out by obtaining sectional images which are vertical to the main surface of a printed circuit board (so-called vertical sectional images), and not by obtaining sectional images which look as if the printed circuit board had been sliced in a direction parallel to the main surface thereof (transverse sectional images) as before. By finding a method whereby vertical sectional images can be photographed, and developing an apparatus with which the method can be realized, the present invention was completed.

FIGS. 5(a) and 5(b) are diagrams showing vertical sectional images of a connecting portion. FIG. 5(a) shows a case wherein no defective connection exists, and FIG. 5(b) shows a case wherein open solder balls 1a exist.

A method of X-ray inspection according to the present invention, wherein a section of a sample is photographed using X-rays to be inspected, includes arranging an X-ray source to apply X-rays and an X-ray detecting means to detect X-rays facing each other with the sample in between. An X-ray incidence plane in the X-ray detecting means is made parallel to the section. The X-ray detecting means is swung about a straight line on the same plane with the section as the central axis, with the parallel relationship between the X-ray incidence plane and the section maintained, while applying X-rays to the sample from the X-ray source as the X-ray source is rotated about the straight line on the same plane with the section as the axis of rotation in synchronization with the X-ray detecting means. X-rays passing through the sample in the X-ray detecting means are then detected.

In the method of X-ray inspection, by mutually moving the X-ray source and the X-ray detecting means while a uniform geometric relationship between them is maintained on the basis of a section of the sample as the subject, a section which is a base of the movements is in a state where it can be regarded as being fixed. On the other hand, the more distant other portions are from the base of the movements, the larger the deformation of the images thereof becomes. As a result, the images thereof become obscure, so that they cannot be the subject of visual recognition. Accordingly, a vertical sectional image is successfully obtained.

This principle is described below using diagrams in FIGS. 6–8, provided for describing the method of X-ray inspection. FIGS. 6, 7 and 8 show a plan view, a front view, and a side view, respectively. FIG. 9 is a perspective view diagrammatically showing a sample.

In the figures, reference numeral 13 represents a sample, and the sample 13 is placed on a stage 14 (FIG. 7). The diagonally shaded area 13a (FIG. 9) represents a section of the sample 13 that is to be the subject. Points A, B, D, E and F are on the section 13a. The points B, A and D are on the same straight line $L_1$, the points E, A and F are on the same straight line $L_2$, and the straight lines $L_1$ and $L_2$ intersect at right angles. A point K in the sample 13 is not on the section 13a but is located at a distance m from the point B on the section 13a.

An X-ray source 11 and an X-ray detecting means 12 are arranged so as to face each other with the sample 13 in between. X-rays are emitted from the X-ray source 11 and X-rays passing through the sample 13 are detected in the X-ray detecting means 12.

(A) By making an X-ray incidence plane 12a in the X-ray detecting means 12 parallel to the section 13a in the sample 13, the points A, B, D, E and F on the section 13a are projected at points a, b, d, e and f on the X-ray incidence plane 12a in the X-ray detecting means 12 located at H (FIGS. 6–8), respectively. Here, the point a is the center of the X-ray incidence plane 12a.

(B) The X-ray detecting means 12 is swung or orbited about the straight line L, as a central axis with the parallel relationship between the X-ray incidence plane 12a and the section 13a maintained. The X-ray source 11 is rotated or pivoted about the straight line $L_1$ as the axis of rotation or pivot axis in synchronization with the X-ray detecting means 12. By this operation, the X-ray source 11 moves to g from G, and the X-ray detecting means 12 moves while staying in a position parallel to itself (swings) to h from H.

(C) The points A, B, D, E and F on the section 13a are projected at points a, b, d, e and f on the X-ray incidence plane 12a in the X-ray detecting means 12 located at h, respectively.

As is obvious from FIGS. 6 and 7, distances $r_1$, $r_2$, $r_3$ and $r_4$ between the point a and the points b, d, e and f in the X-ray incidence plane 12a are not changed by the movements (B). The scale of geometric enlargement of each point A, B, D, E or F on the section 13a to the X-ray incidence plane 12a is uniform, and the below relationship is formed.

The scale of geometric enlargement

=Ga/GA=Gb/GB=Gd/GD=Ge/GE=Gf/GF

=ga/gA=gb/gB=gd/gD=ge/gE=gf/gF

The point K located at a distance m from the section 13a is projected at a point $k_H$ on the X-ray incidence plane 12a located at H, and is projected at a point $k_h$ on the X-ray incidence plane 12a located at h. A gap of a distance $r_5$ is generated between the positions where the point K is projected during the movements (B). As a result, the image becomes obscure. The picture flows and is not fixed.

In the method of X-ray inspection, a picture which can be obtained from the X-ray detecting means 12 takes the form of the section 13a including the straight line $L_1$ and having a parallel relationship with the X-ray incidence plane 12a. In other words, a sectional image of the section 13a including the straight line $L_1$ which is the axis of rotation of the X-ray source 11 and the central axis of the X-ray detecting means 12 and having a parallel relationship with the X-ray incidence plane 12a can be obtained.

Therefore, when a printed circuit board 2 on which a BGA 1 is mounted (see FIG. 2) is placed on the stage 14 and the condition of mounting of the BGA 1 on the printed circuit board 2 is inspected, a sectional image including the straight line $L_1$ and having a parallel relationship with the X-ray incidence plane 12a, a so-called vertical sectional image (see FIG. 5) can be obtained. Using this image, the detection of open terminals (solder balls) can be certainly carried out, and whether the connection condition in the connecting portion, which is hidden from sight by the package itself, is good or bad can be precisely judged.

The above-described method of X-ray inspection is most effective in obtaining a vertical sectional image of the printed circuit board 2, considering the movements of the X-ray source 11 and the X-ray detecting means 12. However, when the connection condition is inspected, for example, it is also possible to obtain not only a vertical sectional image vertical to the main surface of the printed circuit board 2, but also a sectional image oblique or horizontal to the main surface of the printed circuit board 2 (a transverse sectional image in the horizontal case).

A section that is to be the subject can be any section vertical to a stage on which the sample is placed. By choosing a section which is vertical to the stage as the subject section, a vertical sectional image (see FIG. 5) can be obtained. But the subject section can also be any section out of vertical to the stage on which the sample is placed. By choosing a section out of vertical to the stage, a sectional image oblique or horizontal to the stage can be obtained.

Preferably the straight line set as the central axis and the axis of rotation is vertical to a stage on which the sample is placed. By setting the straight line vertical to the stage, a vertical sectional image can be obtained most effectively.

An X-ray inspection apparatus according to the present invention has an X-ray source for applying X-rays and an X-ray detecting means or device for detecting X-rays arranged so as to face each other with a sample in between. X-rays emitted from the X-ray source and passing through the sample are detected by the X-ray detecting means. An X-ray incidence plane of the X-ray detecting means is arranged so as to be parallel to a prescribed straight line. A swinging means swings the X-ray detecting means about the straight line as a central axis while the X-ray incidence plane is kept facing in the same direction all of the time. A first rotating means rotates the X-ray source about the straight line as an axis of rotation in synchronization with the X-ray detecting means.

The X-ray source and the X-ray detecting means are arranged so as to face each other with the sample as a subject in between them. The X-ray incidence plane is arranged so as to be parallel to the straight line. The X-ray detecting means is swung about the straight line as a central axis while the X-ray incidence plane is kept facing in the same direction all of the time. X-rays are applied to the sample from the X-ray source as the X-ray source is rotated about the straight line as the axis of rotation in synchronization with the X-ray detecting means, and X-rays passing through the sample are detected by the X-ray detecting means.

When the X-ray source and the X-ray detecting means mutually move with a uniform geometric relationship between them maintained on the basis of a plane including the straight line and having a parallel relationship with the X-ray incidence plane, the plane is a base of movement and is in a state where it can be regarded as being fixed. Therefore, a section of the sample on the plane that is the base of movement becomes a subject of visual recognition. The more distant the other portions are from the base portion, the larger the deformation of the images thereof becomes. As a result, the images thereof become obscure, so that they cannot be subjects of visual recognition. A sectional image of a section of the sample including the straight line and having a parallel relationship with the X-ray incidence plane can thus be obtained. Accordingly, when the mounting condition of a BGA 1 on a printed circuit board 2 on which the BGA 1 is mounted (see FIG. 2) is inspected, a sectional image of the printed circuit board 2 including the straight line and having a parallel relationship with the X-ray incidence plane can be obtained.

A subject section of the sample is on the same plane with a plane including the straight line, and has a parallel relationship with the X-ray incidence plane. The section can preferably be vertical to a stage on which the sample is placed in the X-ray inspection apparatus.

Because a subject section is any section vertical to the stage, a vertical sectional image (see FIG. 5) can be obtained. Using this resultant image, the detection of open solder balls can be certainly carried out, and whether the connection condition of a package on a printed circuit board, which usually hides inside the package, is good or bad can be precisely judged.

A subject section of the sample, being on the same plane with a plane including the straight line and maintaining a parallel relationship with the X-ray incidence plane, can be out of vertical to the stage on which the sample is placed in the X-ray inspection apparatus.

With a subject section being any section except for those vertical to the stage, a sectional image oblique or horizontal to the stage can be obtained. A horizontal sectional image is a transverse sectional image.

The straight line that is the central axis and the axis of rotation is not vertical to a stage on which the sample is placed in the X-ray inspection apparatus. Because the straight line is vertical to the stage, a vertical sectional image can be obtained most effectively.

A sliding mechanism can be provided for the X-ray detecting means for sliding it in a direction vertical to the X-ray incidence plane. Because the X-ray detecting means can be slid in the direction vertical to the X-ray incidence plane, the position of the sectional image can be finely controlled.

A stage transfer means for two-dimensionally transferring a stage on which the sample is placed can also be provided. Because the stage can be two-dimensionally transferred, a desired sectional image can be easily obtained.

According to another aspect of the invention, a second rotating means is provided to rotate the X-ray source about a prescribed straight line as the axis of rotation. A plurality of the X-ray detecting means are arranged with each of the X-ray incidence planes being positioned so as to be able to form a uniform geometric relationship with the rotating X-ray source on the basis of a prescribed plane including the straight line. Because each of the X-ray detecting means is positioned so as to be able to form a uniform geometric relationship with the rotating X-ray source on the basis of a prescribed plane including the straight line, the plane, as a base of movement, is in a state where it can be regarded as being fixed. Therefore, a section of the sample on the base plane can become a subject of visual recognition. The more distant the other portions are from the base, the larger the deformation of the images thereof becomes. As a result, the images thereof become obscure, so that they cannot be subjects of visual recognition. A sectional image of a prescribed section including the straight line can be obtained without transferring the X-ray detecting means.

Accordingly, when the condition of mounting of a BGA on a printed circuit board on which the BGA is mounted (see FIG. 2) is inspected, a sectional image with respect to a prescribed plane including the straight line, which includes the printed circuit board and the BGA, can be obtained.

DESCRIPTION OF THE PREFERRED EMBODIMENTS

Preferred embodiments of an X-ray inspection apparatus according to the present invention are described below by reference to the Figures of the drawings.

Figure 10:
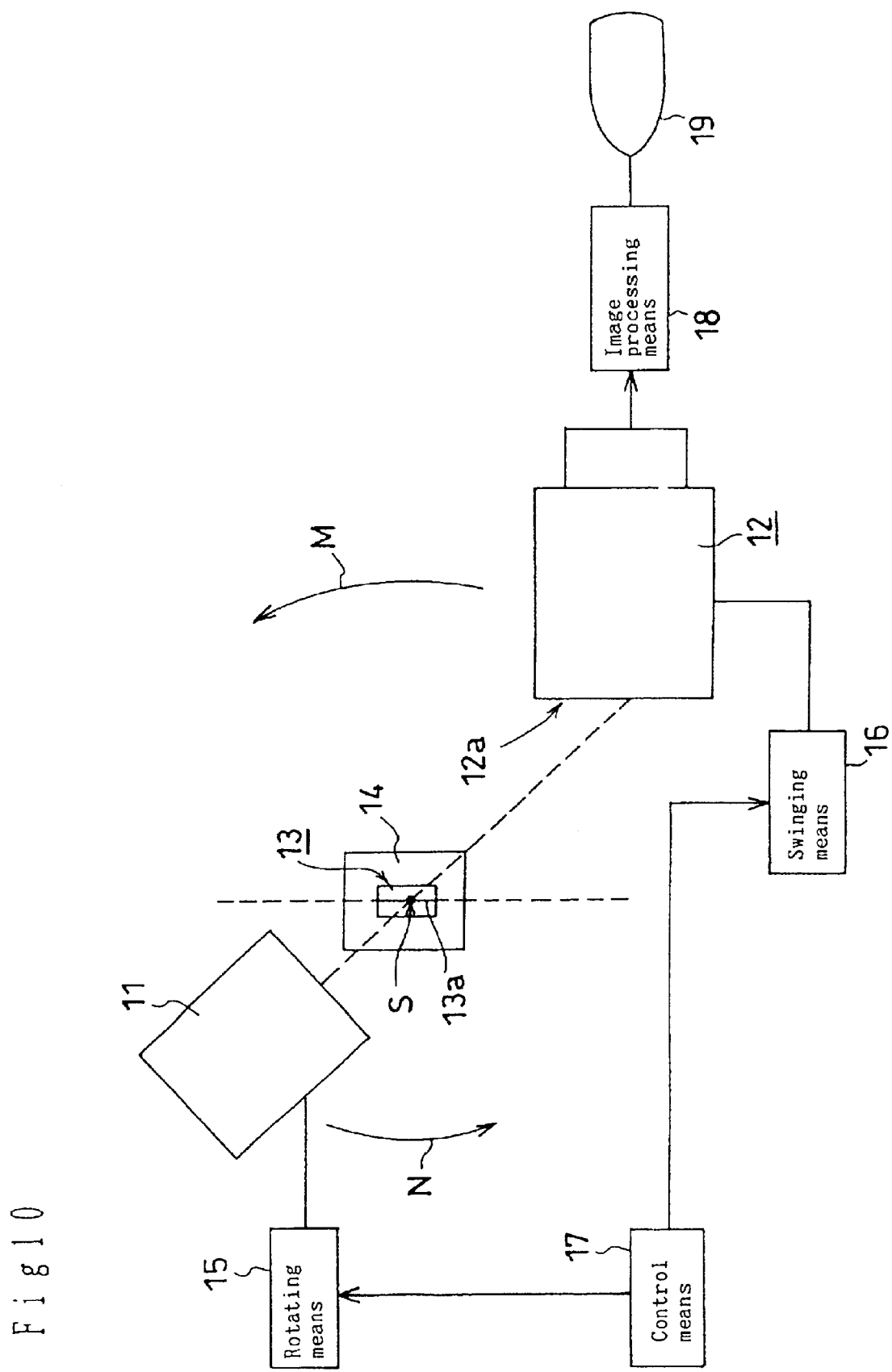
FIG. 10 is a schematic illustration showing the principal part of an X-ray inspection apparatus according to an embodiment (1) of the present invention.

FIG. 10 is a schematic illustration showing a principal part of an X-ray inspection apparatus according to an embodiment of the present invention. In the figure, reference numeral 13 represents a sample, and the sample 13 is placed on a stage 14. Here, in FIG. 10, a direction vertical to the mount surface of the stage 14 is a Z direction, and two directions vertical to the Z direction are X and Y directions. The stage 14 comprises an X-Y table which transmits X-rays, and can be transferred in the X or Y direction by a stage transfer means (not shown) arranged thereunder. Thus, by arranging the stage transfer means under the stage 14, even a sample having a large area such as a mounted board does not interfere with the inspection thereof.

An X-ray source 11 and an X-ray detecting means or device 12 are arranged so as to face each other with the stage 14 between them in the vertical direction (Z direction). X-rays are emitted from the X-ray source 11, and X-rays passing through the sample 13 are detected in the X-ray detecting means 12.

The X-ray source 11 is a microfocus X-ray source of a hermetic tube type having a focus size of 7 μm or so and an outgoing angle of 40° or so. By realizing a minute X-ray focus, a distinct picture can be obtained even if the image picture is enlarged.

The X-ray detecting means 12 is arranged so that an X-ray incidence plane 12a thereof is parallel to an axis S going in the direction vertical to the stage 14 (Z direction). The X-ray detecting means 12 is connected to a swinging means or device 16. It swings in the direction shown by an arrow M about the axis S as the central axis in response to the operation of the swinging means 16 and with the X-ray incidence plane 12a facing in the same direction all of the time.

The X-ray source 11 is connected to a rotating means 15. It rotates in the direction shown by an arrow N in synchronization with the X-ray detecting means 12 about the axis S as the axis of rotation in response to the operation of the rotating means 15. The operation of the rotating means 15 and swinging means 16 with respect to the X and Y directions are controlled by a control means 17 storing a transfer program.

Figure 11:
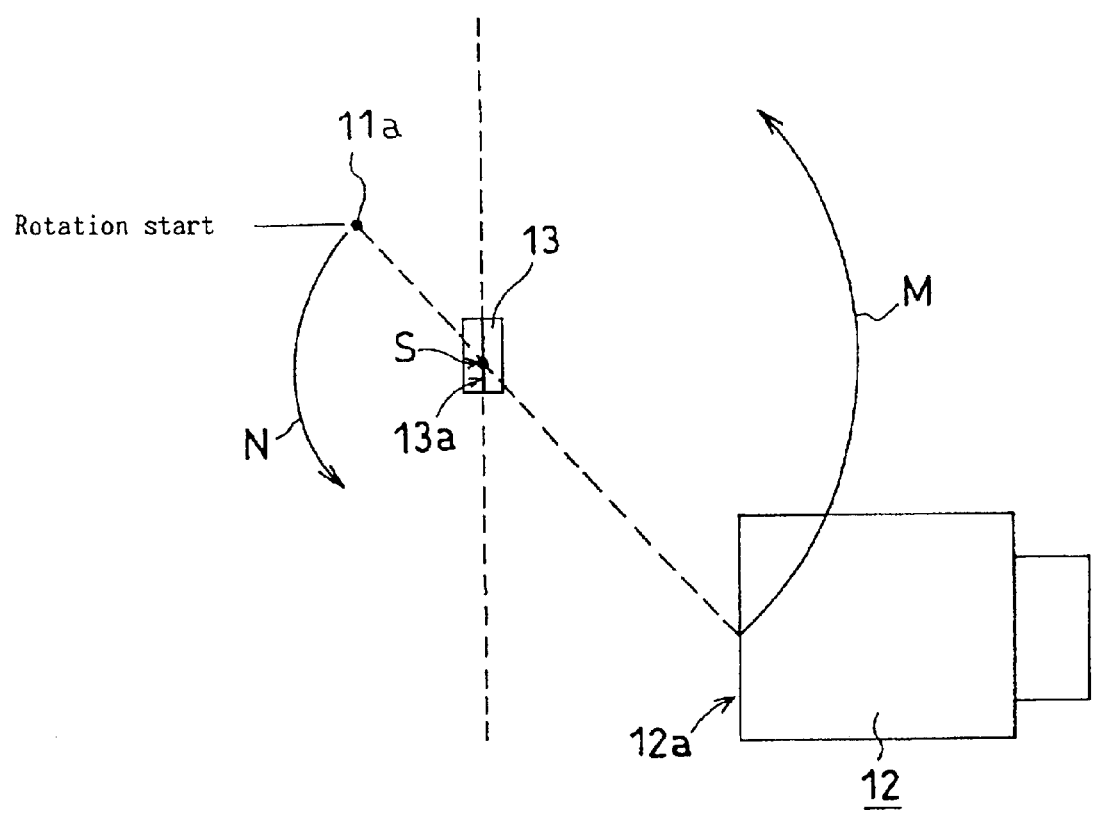
FIG. 11 is a diagram showing the state of movements of an X-ray source and an X-ray detecting means.

The state of movements of the X-ray source 11, which rotates about the axis S as the axis of rotation, and the X-ray detecting means 12, which swings about the axis S as a central axis, is described below using diagrams in FIGS. 11–13. In the figures, reference numeral 11a represents an X-ray focus of the X-ray source 11. FIG. 11 shows a state at the time of start of movement, while FIG. 13 shows a state at the time of stop of movement.

Figure 12:
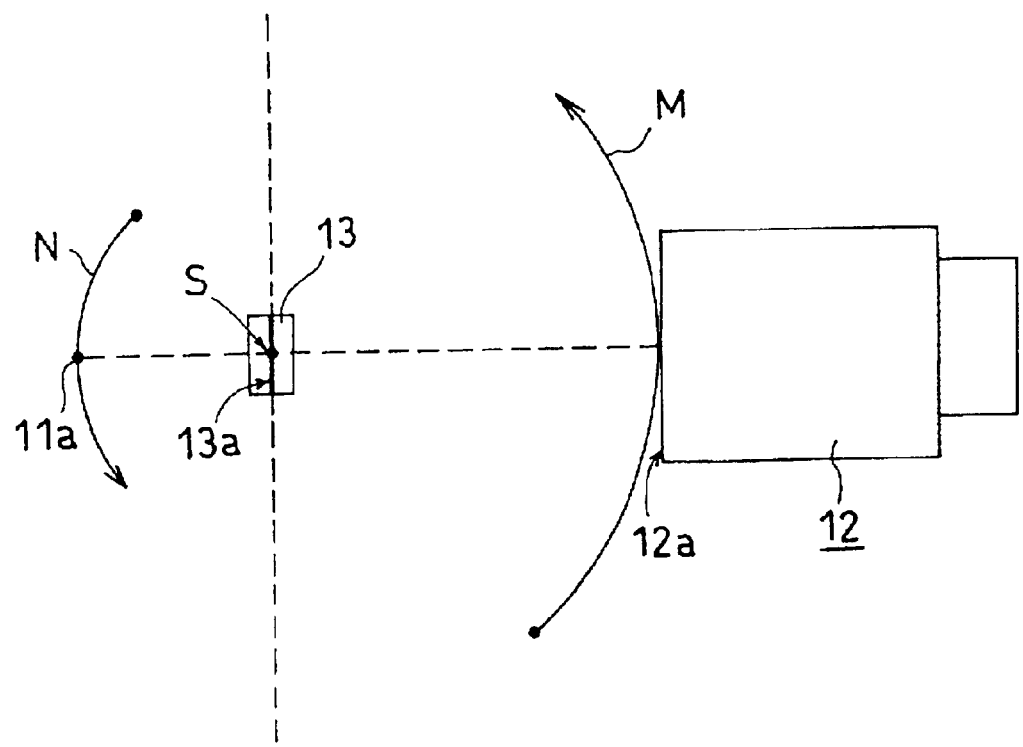
FIG. 12 is a diagram showing the state of movements of an X-ray source and an X-ray detecting means.
Figure 13:
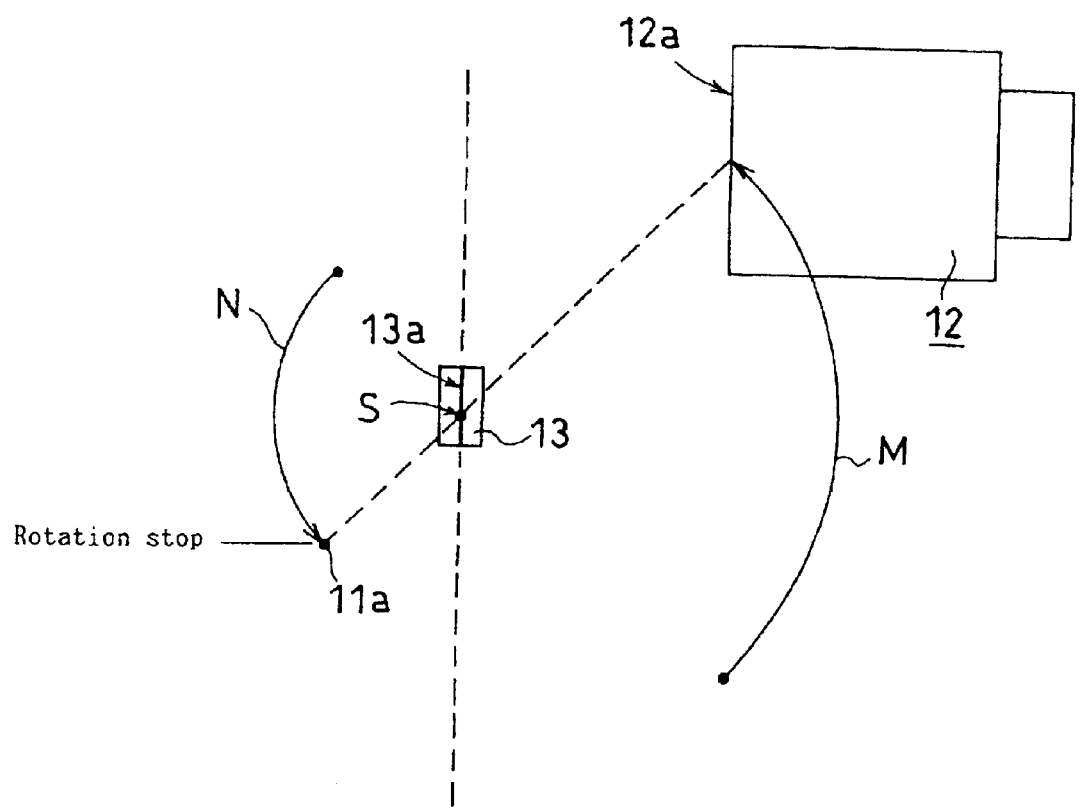
FIG. 13 is a diagram showing the state of movements of an X-ray source and an X-ray detecting means.

As shown in FIGS. 11–13, when the X-ray focus 11a (X-ray source 11) and the X-ray detecting means 12 are moved in synchronization with each other with a uniform geometric relationship maintained, a section 13a of the sample 13 including the axis S, and having a parallel relationship with the X-ray incidence plane 12a, is in a state where it can be regarded as being fixed. The details are described in the SUMMARY OF THE INVENTION.

The X-ray detecting means 12 is connected to an image processing means 18 (FIG. 10), to which image data (picture signals) corresponding to the detected X-rays are outputted.

The image processing means 18 starts image integrating processing at the same time as the start of the movements, and performs the integrating processing a predetermined member of times (e.g. 256 times) by the time movement is stopped so as to improve the image quality so that a processed image (static image) is displayed on a monitor 19. The processed image represents a sectional image on the section 13a of the sample 13 as described above.

In the X-ray inspection apparatus according to the embodiment, the X-ray source 11 and the X-ray detecting means 12 are arranged so as to face each other with the sample 13 as a subject therebetween, and the X-ray incidence plane 12a is arranged so as to be parallel to the axis S extending in a direction vertical to the stage 14. The X-ray detecting means 12 is swung about the axis S as the central axis, with the X-ray incidence plane 12a therein facing in the same direction all of the time, while the X-ray source 11 irradiates the sample 13 with X-rays while being rotated about the axis S as the axis of rotation in synchronization with the X-ray detecting means 12. X-rays passing through the sample 13 are detected in the X-ray detecting means 12.

Figure 1:
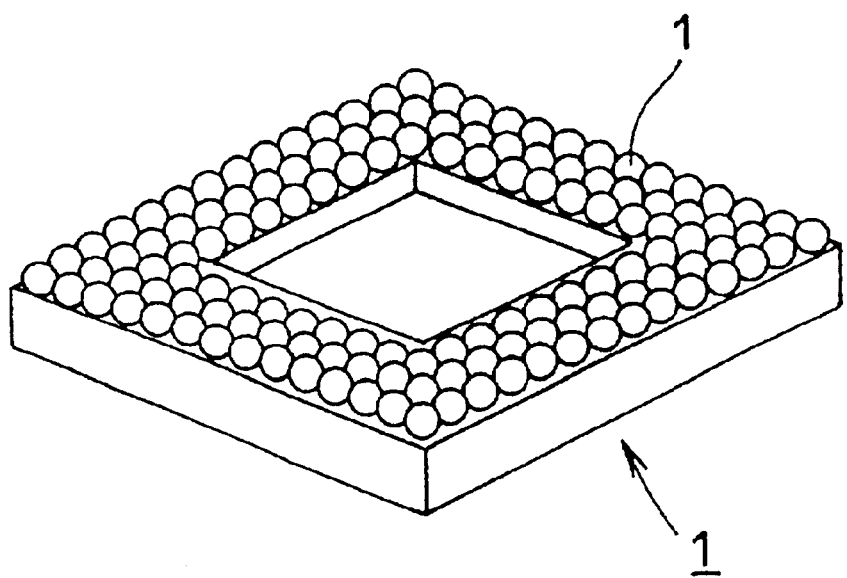
FIG. 1 is a perspective view of a BGA seen from the side of terminals.
Figure 2:
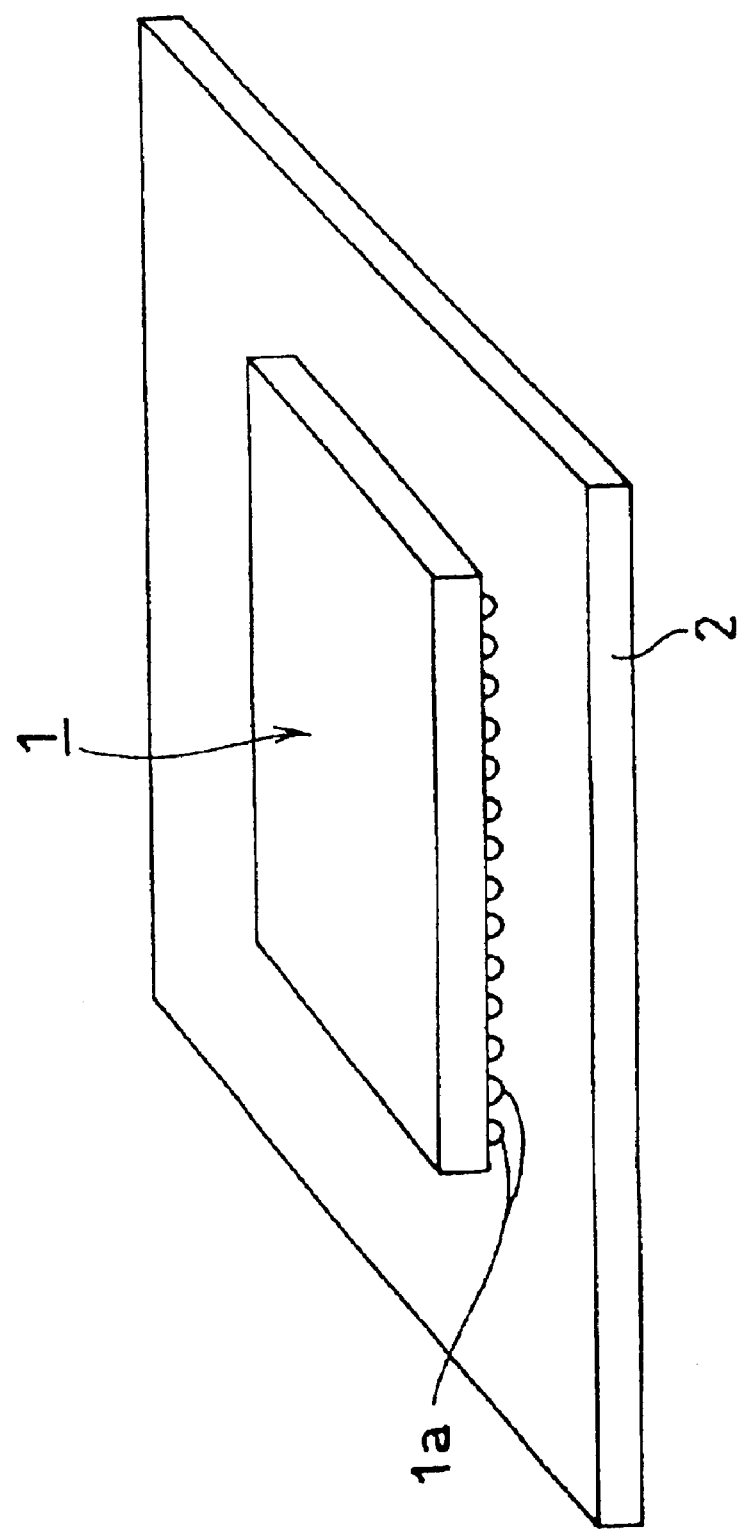
FIG. 2 is a perspective view showing a printed circuit board in a situation where a BGA is mounted thereon.
Figure 5:
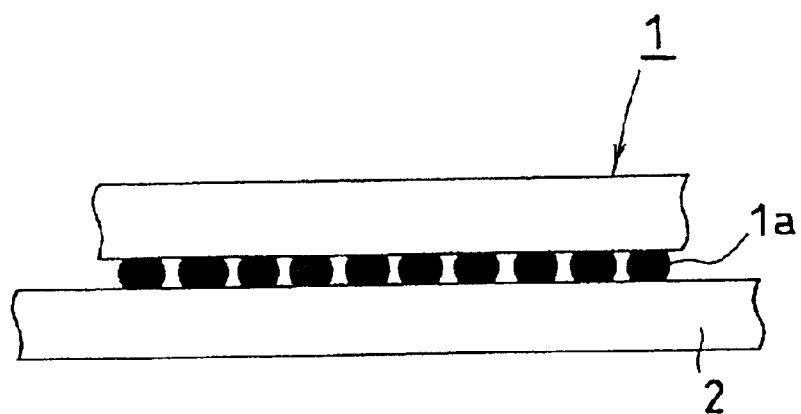
FIGS. 5(a) and 5(b) are diagrams showing vertical sectional images of a connecting portion of a BGA and a printed circuit board.
Figure 5:
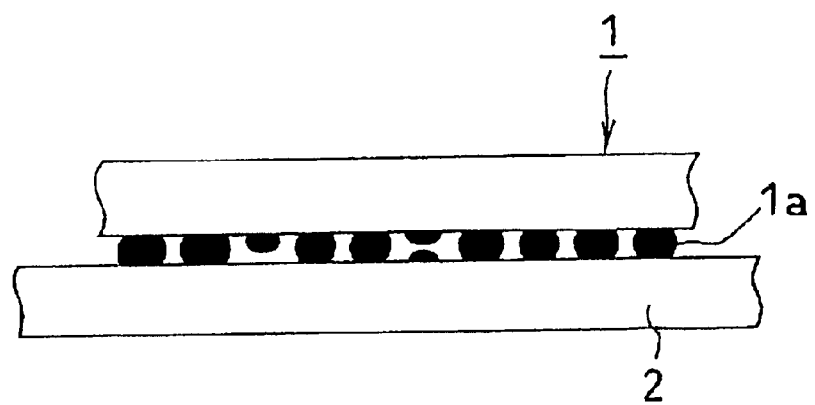
Figure 6:
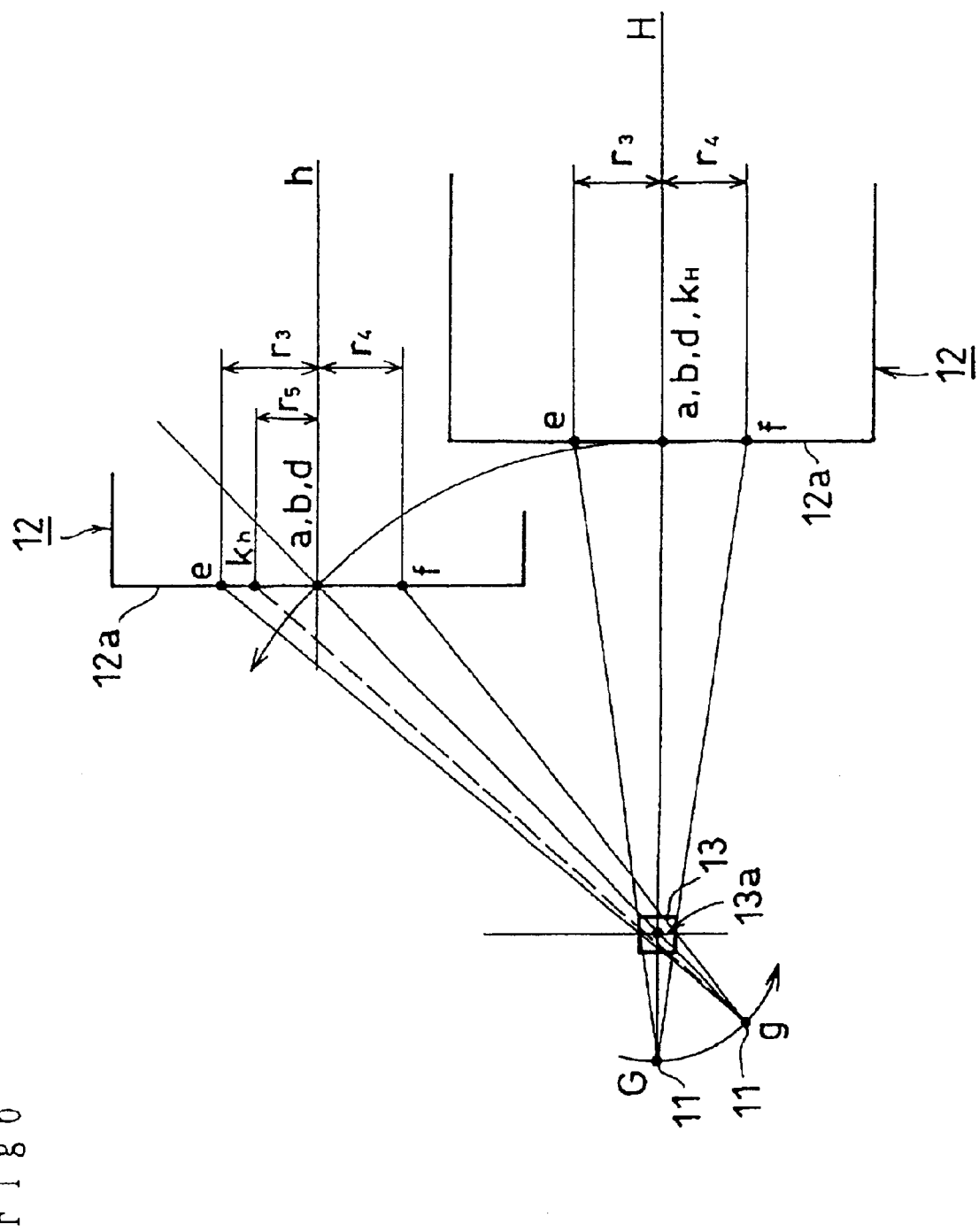
FIG. 6 is a plan view illustrating a method of X-ray inspection according to the present invention.
Figure 7:
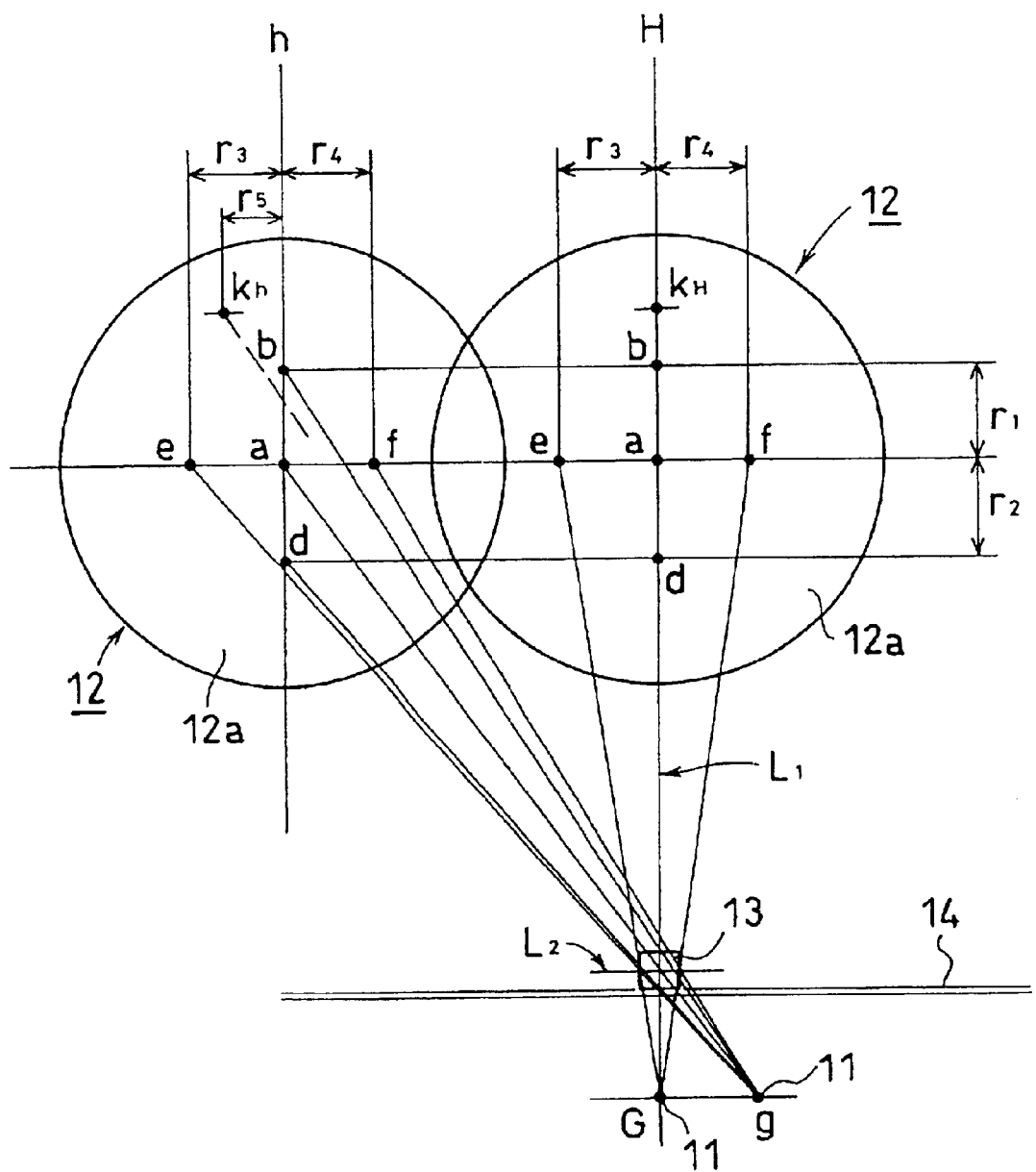
FIG. 7 is a front view illustrating the method of X-ray inspection according to the present invention.
Figure 8:
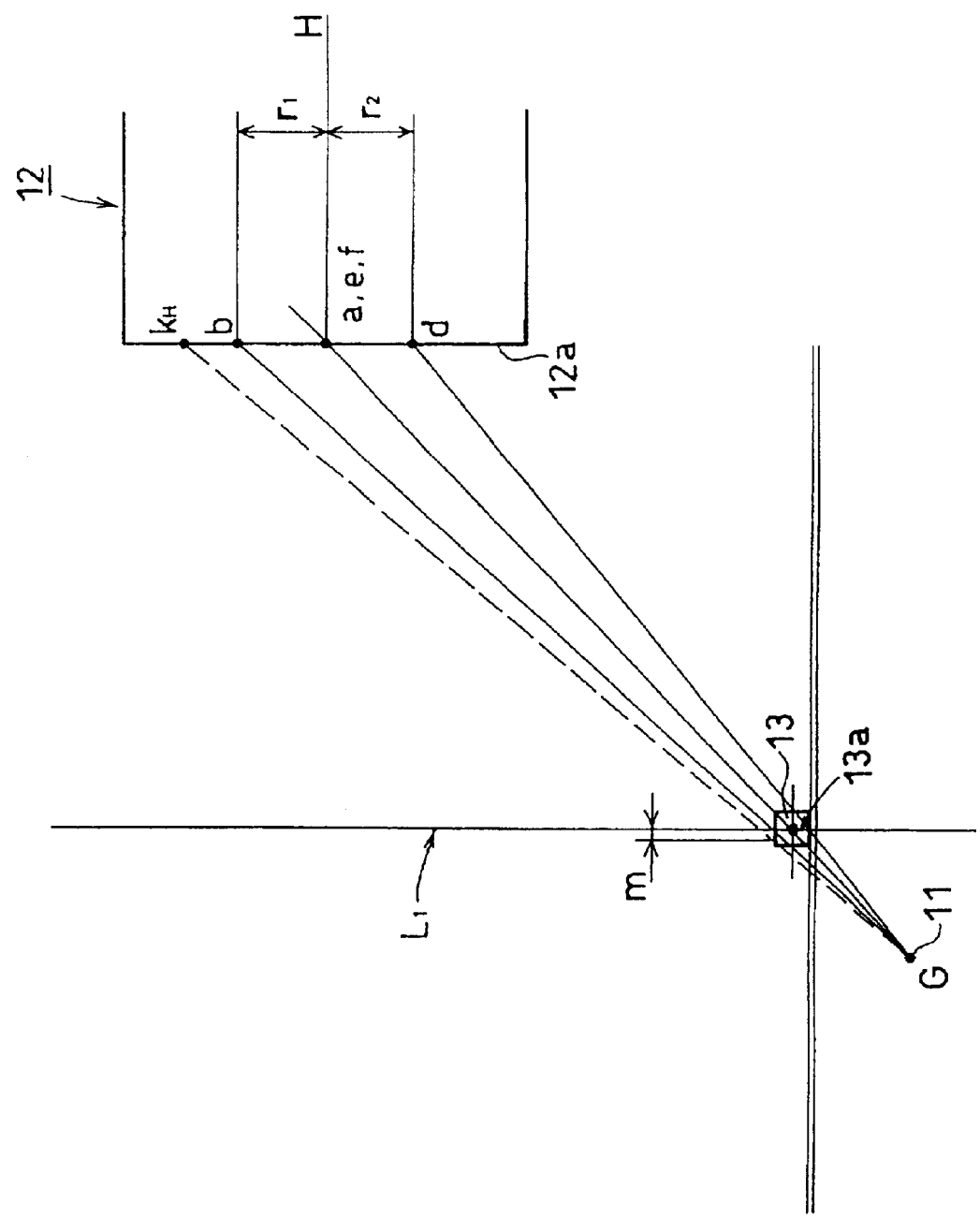
FIG. 8 is a side view shown illustrating the method of X-ray inspection according to the present invention.
Figure 9:
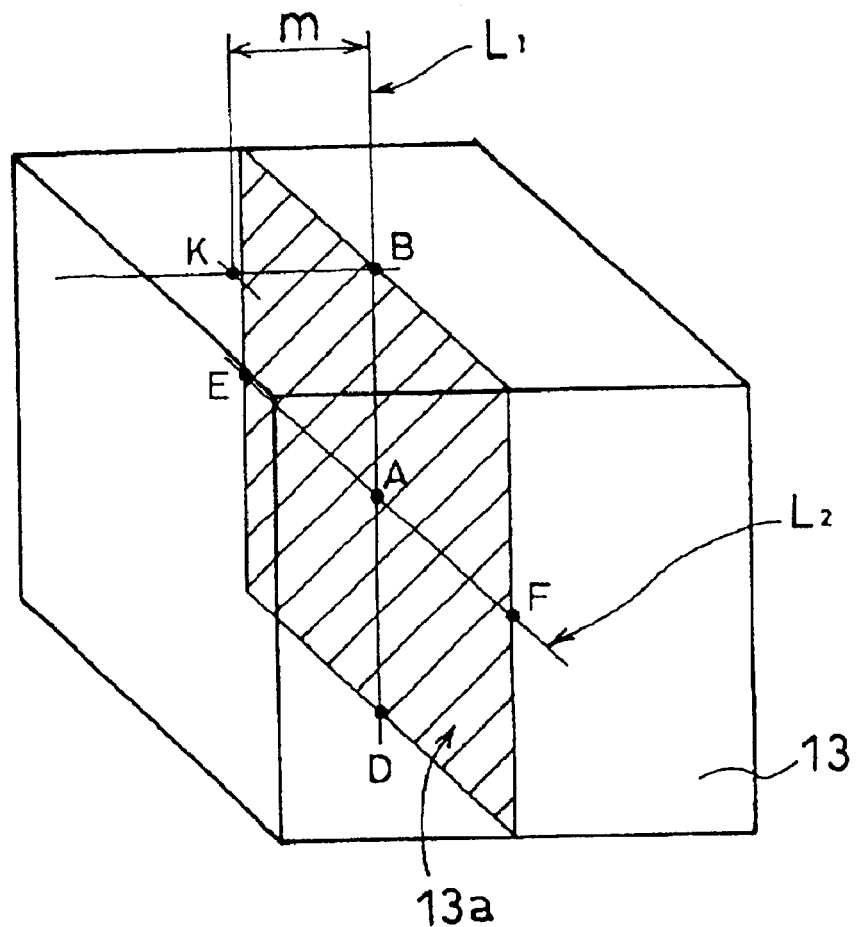
FIG. 9 is a perspective diagram of a sample.

As described above, when the X-ray source 11 and the X-ray detecting means 12 are mutually moved with a uniform geometric relationship being maintained, the section 13a, as a base of the movement, is in a state where it can be regarded as being fixed. The more distant the other portions are from the base of the movement, the larger the deformation of the images thereof becomes. As a result, the images thereof become obscure so that they cannot be subjects of visual recognition. Consequently, a sectional image of the section 13a including the axis S, which is the axis of rotation of the X-ray source 11 and the central axis of the X-ray detecting means 12 and has a parallel relationship with the X-ray incidence plane 12a, can be obtained. Therefore, when a printed circuit board 2 having a BGA 1 is mounted thereon (see FIG. 2) is placed on a stage 14 and the mounting condition of the BGA 1 on the printed circuit board 2 is inspected, a vertical sectional image (see FIG. 5) including the axis S and having a parallel relationship with X-ray incidence plane 12a can be obtained. Using this, the detection of open connections of solder balls 1a can be certainly carried out, and whether the connection condition of the connecting portion that is usually hidden from sight and outside observation by the package itself is good or bad can be precisely judged.

Figure 3:
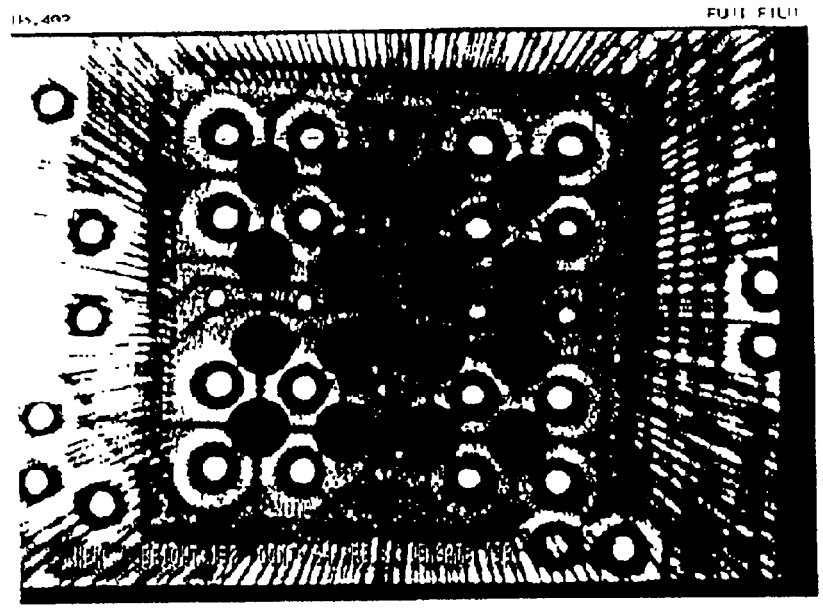
FIGS. 3(a) and 3(b) are X-ray photographs of a connecting portion of a BGA and a printed circuit board.
Figure 3:
Figure 4:
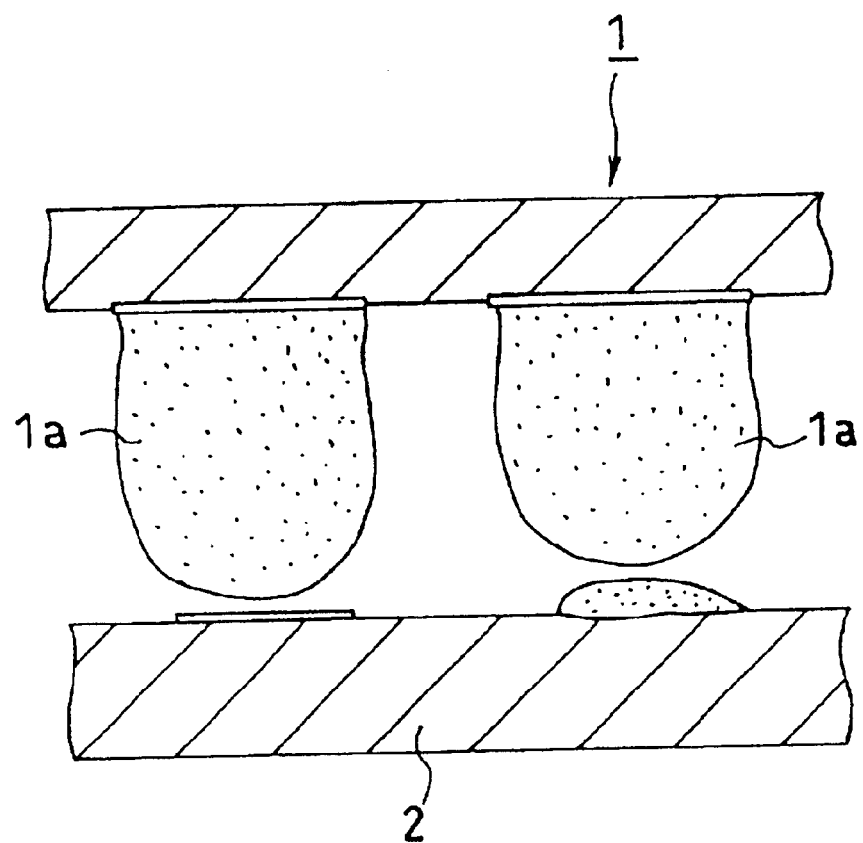
FIG. 4 is a diagram showing an open state of solder balls.

When only simple image improvement processing is performed in the image processing means 18, without processing to obtain a sectional image being performed, it also becomes possible to observe a perspective image of a sample 13, seen from an oblique direction (see e.g. FIG. 3), using the X-ray inspection apparatus shown in FIG. 10. When the image improvement processing is performed in the inspection of the mounting condition of an electronic device on a printed circuit board 2, the observation of a perspective image oblique to the main surface of the printed circuit board 2 makes it possible to first find likely places where defective connections might occur. Then, the observation using a vertical sectional image is only needed to be conducted in the likely places. As a result, inspection efficiency can be greatly enhanced.

In the X-ray inspection apparatus according to the embodiment, the axis S is set in a direction vertical to the stage 14, but in another embodiment, it is also possible to set the axis S in any direction (oblique or horizontal) to the stage 14 other than the vertical direction. For example, when the X-ray incidence plane 12a is arranged so as to be parallel to the axis S extending in a direction oblique to the stage 14, the X-ray detecting means 12 is swung about the axis S as the central axis with the X-ray incidence plane 12a facing in the same direction all of the time and the X-ray source 11 irradiates the sample 13 with X-rays while being rotated about the axis S as the axis of rotation. X-rays passing through the sample 13 are detected in the X-ray detecting means 12, and a sectional image with respect to a plane inclined to the vertical direction can be obtained.

When the axis S is set on the same plane as the surface of the stage 14, a sectional image (transverse sectional image) of a section on which the sample 13 is sliced horizontally can be obtained.

In the above-described X-ray inspection apparatus, the X-ray detecting means 12 is swung about the axis S as the central axis with the X-ray incidence plane 12a therein facing in the same direction all of the time (the X-ray detecting means 12 swings as shown in FIGS. 11–13) and the X-ray source 11 irradiates the sample 13 with X-rays while being rotated about the axis S as the axis of rotation. X-rays passing through the sample 13 are detected in the X-ray detecting means 12. But it is also possible to obtain a desired sectional image similarly without transferring the X-ray detecting means 12, by an X-ray detecting means 12 being not swung, but located in each position shown in FIGS. 11–13, for example, so that image data are obtained from plural fixed X-ray detecting means 12.

EXAMPLES

Figure 14:
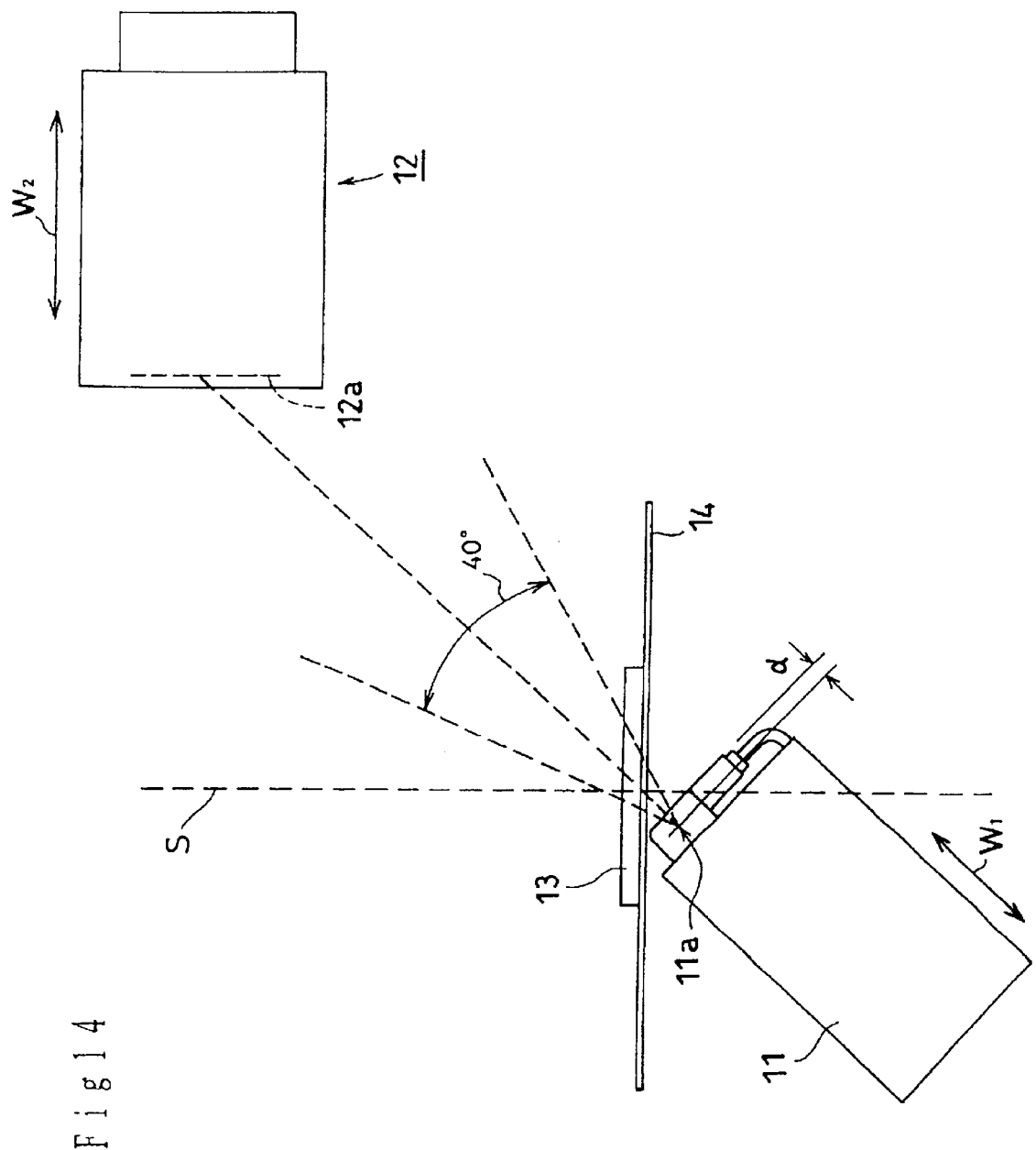
FIG. 14 is a side view partly in section showing the principal part of an X-ray inspection apparatus according to an Example 1.

FIG. 14 is a side view partly in section schematically showing a principal part of an X-ray inspection apparatus according to Example 1. Here, as an X-ray source 11, a microfocus of a hermetic tube type having an X-ray tube voltage of 100 kV, a focus size of 7 μm, an outgoing angle of 40°, and a distance a between its cabinet and its X-ray focus 11a of 9.5 mm is used.

As an X-ray detecting means 12, an image intensifier having high resolution, high contrast, and low noise is used.

A sliding mechanism (not shown) whereby the X-ray source 11 can be slid in the direction shown by an arrow $W_1$ is connected to the X-ray source 11. Using the sliding mechanism, the size of an obtained image can be regulated. For example, when the X-ray source 11 is made close to a sample 13, the scale of geometric enlargement is increased, so that the obtained image can be made larger.

A sliding mechanism (not shown) whereby the X-ray detecting means 12 can be slid in the direction shown by an arrow $W_2$ is connected to the X-ray detecting means 12. Using the sliding mechanism, the limits of the obtained image can be finely regulated. For example, when the X-ray detecting means 12 is made close to the axis S, a sectional image of a section 13a of the sample 13 whose upper portion is cut can be obtained.

By placing a printed circuit board 2 on which a BGA 1 is mounted (see FIG. 2) as a sample 13 on a stage 14, a vertical sectional image (see FIG. 5) can be obtained. Using this, the detection of open connections of solder balls 1a can be certainly carried out, and whether the connection condition of the connecting portion, which is usually hidden from sight and outside observation by the package itself, is good or bad can be precisely judged.

Since the microfocus of a hermetic tube type has an outgoing angle of 40°, the X-ray source 11 is tilted so that X-rays emitted from the X-ray source 11 enter an X-ray incidence plane 12a in the X-ray detecting means 12. When the X-ray source 11 is tilted, the distance between the X-ray focus 11a and the sample 13 becomes longer. The scale of geometric enlargement becomes a little smaller than that in the case where the X-ray focus 11a is brought into intimate contact with the sample 13, but it causes no special problems for industrial use.

When the microfocus is not of a hermetic tube type, but of an open tube type, a microfocus having a focus size of 2 μm, an outgoing angle of 120°, and a distance between its cabinet and its X-ray focus of 1 mm can be realized. When it is adopted as the X-ray source 11, the X-ray source 11 does not need to be tilted, and the distance between its cabinet and its X-ray focus is nearly 10 times shorter than that of the microfocus of a hermetic tube type, so that the scale of enlargement can be extensively improved.

What is claimed is:

1. A method of X-ray inspection of a vertical section of a sample, comprising:

arranging an X-ray source and an X-ray detecting device so as to face each other with the sample between them;

swinging the X-ray detecting device in translational motion about a vertical straight line as an axis, the vertical straight line lying in a plane of the vertical section of the sample, while maintaining an incidence plane of the X-ray detecting device parallel to the vertical section of the sample;

applying X-rays to the sample with the X-ray source while rotating the X-ray source about the straight line in synchronization with said swinging of the X-ray detecting device; and detecting X-rays passing through the sample with the X-ray detecting device to produce a vertical sectional image of the sample.

2. The method of claim 1, wherein the sample is placed on a stage and the section of the sample is vertical to the stage.

3. The method of claim 1, wherein the sample is placed on a stage and the straight line is vertical to the stage.

4. An X-ray inspection apparatus, comprising:

an X-ray source;

an X-ray detecting device operable to detect X-rays, wherein said X-ray detecting device and said X-ray source are positioned relative to each other so that a sample can be placed there between and so that X-rays emitted from said source to pass through a sample can be detected by said X-ray detecting device to produce a vertical sectional image of the sample, said X-ray detecting device having an X-ray incidence plane arranged to be parallel to a vertical straight line;

a swinging means for swinging said X-ray detecting device in translational motion about the straight vertical line as an axis while said X-ray incidence plane is maintained facing in the same direction; and a rotating means for rotating said X-ray source about the vertical straight line as an axis of rotation in synchronization with said X-ray detecting device.

5. The apparatus of claim 4, wherein:

a stage is located between said X-ray detecting device and said X-ray source for having the sample placed thereon such that a subject section of the sample is in a plane containing the straight line and parallel to said X-ray incidence plane; and the section is vertical to said stage.

6. The apparatus of claim 5, wherein the straight line is vertical to said stage.

7. The apparatus of claim 4, wherein the straight line is vertical to said stage.

8. The apparatus of claim 4, and further comprising a sliding mechanism for sliding said X-ray detecting device in a direction perpendicular to said X-ray incidence plane.

9. The apparatus of claim 8, and further comprising a stage transfer device for two-dimensionally transferring a stage on which the sample is placed.

10. The apparatus of claim 4, and further comprising a stage transfer device for two-dimensionally transferring a stage on which the sample is placed.

* * * * *